United States Patent
Qu et al.

(10) Patent No.: US 12,228,215 B2
(45) Date of Patent: Feb. 18, 2025

(54) CHECK VALVE FOR VENTILATOR

(71) Applicant: RESVENT MEDICAL TECHNOLOGY CO., LTD, Shenzhen (CN)

(72) Inventors: Kai Qu, Shenzhen (CN); Rongrong Zhu, Shenzhen (CN)

(73) Assignee: RESVENT MEDICAL TECHNOLOGY CO., LTD, Shenzhen (CN)

( * ) Notice: Subject to any disclaimer, the term of this patent is extended or adjusted under 35 U.S.C. 154(b) by 23 days.

(21) Appl. No.: 18/485,287

(22) Filed: Oct. 11, 2023

(65) Prior Publication Data

US 2024/0200677 A1    Jun. 20, 2024

(30) Foreign Application Priority Data

Dec. 16, 2022   (CN) .......................... 202211627615.8

(51) Int. Cl.
*F16K 15/14*       (2006.01)
*F16K 27/02*       (2006.01)
*A61M 16/20*       (2006.01)

(52) U.S. Cl.
CPC ........ *F16K 15/147* (2013.01); *F16K 27/0209* (2013.01); *A61M 16/208* (2013.01)

(58) Field of Classification Search
CPC .. F16K 15/147; F16K 27/0209; F16K 15/144; F16K 47/08; A61M 16/208
See application file for complete search history.

(56) References Cited

U.S. PATENT DOCUMENTS

| | | | | |
|---|---|---|---|---|
| 3,086,549 | A  * | 4/1963 | Fino ...................... | F16K 15/147 55/420 |
| 2006/0037648 | A1* | 2/2006 | Krishnamoorthy .... | B60K 15/04 137/592 |
| 2009/0126575 | A1* | 5/2009 | Son ..................... | F01M 13/0011 96/189 |
| 2023/0087568 | A1* | 3/2023 | Lemon .................. | F16L 11/133 290/53 |
| 2023/0101175 | A1* | 3/2023 | Flatness ................ | F16K 15/148 392/449 |
| 2023/0250894 | A1* | 8/2023 | Li ........................ | G05D 16/028 414/217 |

\* cited by examiner

*Primary Examiner* — P. MacAde Nichols (57) ABSTRACT

A check valve for a ventilator includes a housing assembly defining a flow channel and a flow guide assembly. The flow channel defines an air outlet. The flow guide assembly is disposed in the flow channel. The flow guide assembly includes a first baffling sleeve and a second baffling sleeve that are disposed in an axial direction of the flow channel in sequence. A first flow passing opening is defined in the first baffling sleeve. One side of the first baffling sleeve away from the first flow passing opening is inclined toward the air outlet. One side of the second baffling sleeve is inclined toward the air outlet. The second baffling sleeve faces the first flow passing opening. A projection of the second baffling sleeve completely overlaps a projection of the first flow passing opening on the horizontal cross section of the flow channel.

10 Claims, 5 Drawing Sheets

CHECK VALVE FOR VENTILATOR

TECHNICAL FIELD

The present disclosure relates to a technical field of medical devices, in particular to a check valve for a ventilator.

BACKGROUND

Ventilators are vital medical devices that prevent and treat respiratory failure, reduce complications, save and prolong life of patients. In modern clinical medicine, the ventilators, as an effective means to replace a spontaneous ventilation function, are widely used in the respiratory failure caused by various reasons, anesthesia respiratory management during major surgery, respiratory support treatment, and first-aid resuscitation, which occupy a very important position in a field of medicine. A ventilator generally needs to connect to an external humidifier when in use. During the patient's breathing, a direction of air changes. When the patient inhales, the air is sent out from an inhaling branch of the ventilator, passes through the external humidifier, and reaches the patient. During the process, the external humidifier warms and humidifies the air. When the patient exhales, the ventilator stops supplying the air, and due to expiratory end pressure in an exhaling branch or an exhaust hole of the ventilator, a part of the air exhaled by the patient enters the inhaling branch through the external humidifier. The part of the air entering the inhaling branch contacts a pipe wall thereof having a lower temperature, and water vapor in the part of the air condenses into condensed water on the pipe wall. The condensed water is then blown into an interior of the ventilator by the air, leading to invalidation of internal components of the ventilator under long-term erosion of the condensed water, and affecting service life of the ventilator.

In the prior art, a diaphragm-type check valve is adopted to prevent the condensed water from entering the internal components of the ventilator. One-way flow of the air is realized by fixing a silicone diaphragm on a support of the ventilator. Specifically, the silicone diaphragm is fixed on one side of the support. When the patent inhales, the silicone diaphragm is blown to open, and when the patent exhales, the silicone diaphragm is pressed against the support for sealing, so as to realize check ventilation.

However, there are some main problems in the prior art. Since the check ventilation is realized through opening and closing between the silicone diaphragm and the support, when the silicone diaphragm is opened and closed repeatedly, the silicone diaphragm repeatedly impacts on the support, which increases a noise of the ventilator and affects actual use experience of the ventilator. Further, in order to realize a quick response of the silicone diaphragm and reduce a resistance of the silicone diaphragm to the air, a thickness of the silicone diaphragm is generally thin, so the silicone diaphragm may be damaged after long-term use. Once the silicone diaphragm is damaged, the silicone diaphragm is unable to prevent reverse flow of the air, which seriously limits the service life of the ventilator and brings certain safety hazards to the patients.

SUMMARY

In order to solve defects, such as high noise and easy damage of a diaphragm-type check valve in a ventilator in the prior art, the present disclosure proposes a check valve for the ventilator.

The check valve for the ventilator comprises a housing assembly and a flow guide assembly. The housing assembly defines a flow channel, and the flow channel defines an air outlet. The flow guide assembly is disposed in the flow channel. The flow guide assembly comprises a first baffling sleeve and a second baffling sleeve. The first baffling sleeve and the second baffling sleeve are disposed in an axial direction of the flow channel in sequence. A first flow passing opening is defined in the first baffling sleeve. One side of the first baffling sleeve away from the first flow passing opening is inclined toward the air outlet. One side of the second baffling sleeve is inclined toward the air outlet. The second baffling sleeve faces the first flow passing opening. A projection of the second baffling sleeve on a horizontal cross section of the flow channel completely overlaps a projection of the first flow passing opening on the horizontal cross section of the flow channel.

Furthermore, the flow channel further defines an air inlet. The first baffling sleeve comprises a first baffling plate. The first flow passing opening is formed between the first baffling plate and an inner wall of the first baffling sleeve. The first baffling plate is arc-shaped. An outer arc surface of the first baffling plate faces the air inlet, and an inner arc surface of the first baffling plate faces the air outlet.

Furthermore, the first baffling sleeve further comprises at least one first rectifying plate. The first baffling plate is close to the air inlet. The at least one first rectifying plate is close to the air outlet. The at least one first rectifying plate is located in a middle of the flow channel. A second flow passing opening is formed between a first side surface of the at least one first rectifying plate and the inner wall of the first baffling sleeve. A third flow passing opening is formed between a second side surface of the at least one first rectifying plate and the inner wall of the first baffling sleeve. The second flow passing opening faces the first flow passing opening, and the third flow passing opening faces the first baffling plate.

Furthermore, the second baffling sleeve comprises a second baffling plate. A fourth flow passing opening is formed between the second baffling plate and an inner wall of the second baffling sleeve. The second baffling plate is arc-shaped. An outer arc surface of the second baffling plate faces the air inlet, and an inner arc surface of the second baffling plate faces the air outlet.

Furthermore, the second baffling sleeve further comprises at least one second rectifying plate. The second baffling plate is close to the air inlet. The at least one second rectifying plate is close to the air outlet. The at least one second rectifying plate is located in a middle of the flow channel. A fifth flow passing opening is formed between a first side surface of the at least one second rectifying plate and the inner wall of the second baffling sleeve. A sixth flow passing opening is formed between a second surface of the at least one second rectifying plate and the inner wall of the second baffling sleeve. The fifth flow passing opening faces the fourth flow passing opening, and the sixth flow passing opening faces the second baffling plate.

Furthermore, both an area of a projection of the first flow passing opening and an area of a projection of the fourth flow passing opening on the horizontal cross section of the flow channel are less than one half of an area of the horizontal cross section of the flow channel.

Furthermore, the housing assembly comprises a pipe sleeve and a sealing sleeve. Positioning protrusions are disposed on an outer side of the sealing sleeve. Annular bulges are disposed on two ends of the sealing sleeve. The flow guide assembly is disposed between the annular bulges.

Furthermore, the first baffling sleeve comprises a first outer ring, a first baffling plate, and a first rectifying plate. The first baffling plate and the first rectifying plate are disposed on an inner side of the first outer ring. The first baffling plate and the first rectifying plate are configured to guide air.

The second baffling sleeve comprises a second outer ring, a second baffling plate, and a second rectifying plate. The second baffling plate and the second rectifying plate are disposed on an inner side of the second outer ring. The second baffling plate and the second rectifying plate are configured to guide the air.

An end surface of the first outer ring abuts against an end surface of the second outer ring. The first outer ring and the second outer ring are installed in the sealing sleeve.

Furthermore, the first outer ring comprises a first baffling outer ring and a first rectifying outer ring. The first baffling plate is disposed in the first baffling outer ring. The first rectifying plate is disposed in the first rectifying outer ring.

The second outer ring comprises a second baffling outer ring and a second rectifying outer ring. The second baffling plate is disposed in the second baffling outer ring. The second rectifying plate is disposed in the second rectifying outer ring.

The first baffling outer ring and the second baffling outer ring are baffling outer ring standard parts. A deviation between an axis of the first baffling outer ring and an axis of the second baffling outer ring is 180 degrees. The first rectifying outer ring and the second rectifying outer ring are rectifying outer ring standard parts. A deviation between an axis of the first rectifying outer ring and an axis of the second rectifying outer ring is 180 degrees.

Furthermore, each of the baffling outer ring standard parts comprise two positioning protrusions respectively disposed on two circumferential surfaces of each of the baffling outer ring standard parts. The two positioning protrusions of each of the baffling outer ring standard parts are symmetrically disposed with respect to a horizontal cross section of each of the baffling outer ring standard parts. Each of the rectifying outer ring standard parts comprise two positioning grooves respectively defined on two circumferential surfaces of each of the rectifying outer ring standard parts. The two positioning grooves of each of the rectifying outer ring standard parts are symmetrically disposed with respect to a horizontal cross section of each of the rectifying outer ring standard parts, and the two positioning grooves of each of the rectifying outer ring standard parts are symmetrically disposed with respect to a vertical cress section of each of the rectifying outer ring standard parts if one of the two positioning grooves of each of the rectifying outer ring standard parts is rotated 180 degrees in an axis direction.

Compared with the prior art, the first baffling sleeve and the second baffling sleeve are disposed in the flow channel of the present disclosure, so through the first baffling sleeve and the second baffling sleeve, the air from the air inlet of the flow channel is smoothly guided to the air outlet. Both the first baffling sleeve and the second baffling sleeve are inclined to the air outlet, the second baffling sleeve faces the first flow passing opening, and the projection of the second baffling sleeve on the horizontal cross section of the flow channel completely overlaps the projection of the first baffling sleeve on the horizontal cross section of the flow channel, which effectively prevent backflow of the air, prevent the air from a humidifier and a patient from flowing backward into the ventilator, effectively prevent water vapor and germs from invading the ventilator, and protect internal components of the ventilator from being corroded by the water vapor or germ contamination.

Further, compared with the prior art, no movable silicone diaphragm is disposed in the present disclosure, and the first baffling sleeve and the second baffling sleeve are fixedly disposed in the flow channel, which effectively reduces the noise of the ventilator, effectively reduces a failure rate of the check valve, improves operation stability of the ventilator, and reduces maintenance cost of the ventilator.

BRIEF DESCRIPTION OF DRAWINGS

In order to clearly describe technical solutions in the embodiments of the present disclosure, the following will briefly introduce the drawings that need to be used in the description of the embodiments or the prior art. Apparently, the drawings in the following description are merely some of the embodiments of the present disclosure, and those skilled in the art are able to obtain other drawings according to the drawings without contributing any inventive labor.

In the drawings: 1—housing assembly; 11—pipe sleeve; 12—sealing sleeve; 121—annular bulge; 2—flow guide assembly; 21—first baffling sleeve; 211—first baffling plate; 212—first flow passing opening; 213—first rectifying plate; 214—second flow passing opening; 215—third flow passing opening; 216—first outer ring; 217—first baffling outer ring; 218—first rectifying outer ring; 22—second baffling sleeve; 221—second baffling plate; 222—fourth flow passing opening 223—second flow rectifying plate; 224—fifth flow passing opening 225—sixth flow passing opening; 226—second outer ring; 227—second baffling outer ring; 228—second rectifying outer ring; 3—flow channel; 31—air inlet; 32—air outlet; 4—baffling outer ring standard part; 41—positioning protrusion; 5—rectifying outer ring standard part; 51—positioning groove.

DETAILED DESCRIPTION

In order to make objectives, technical solutions, and advantages of the present disclosure clearer, the following further describes the present disclosure in detail with reference to accompanying drawings and embodiments. It should be understood that the specific embodiments described here are only used to explain the present disclosure, but not to limit the present disclosure.

Figure 1:
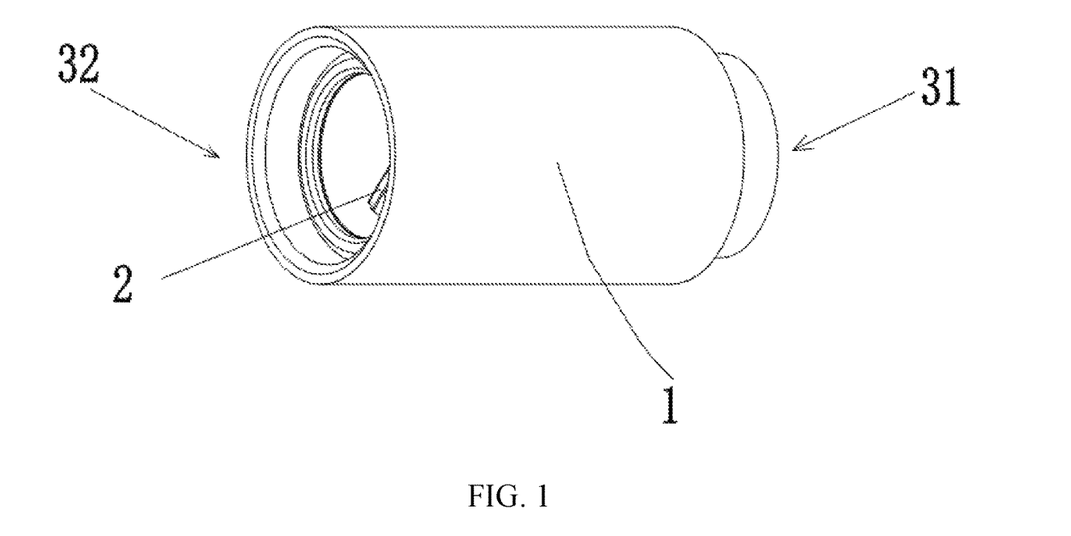
FIG. 1 is a perspective schematic diagram of a check valve of the present disclosure.
Figure 2:
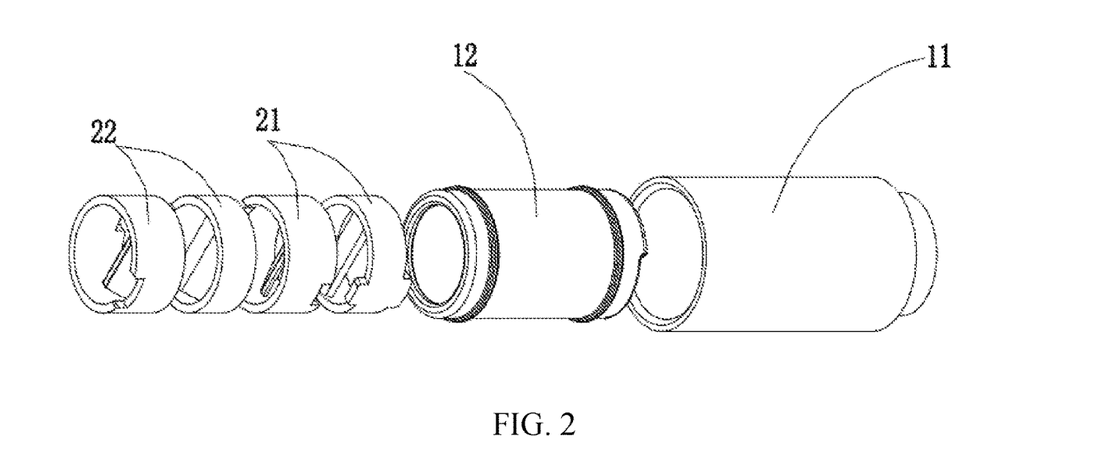
FIG. 2 is an exploded schematic diagram of the check valve of the present disclosure.

The present disclosure provides a check valve for a ventilator. As shown in FIGS. 1 and 2, the check valve for the ventilator comprises a housing assembly 1 and a flow guide assembly 2. The housing assembly 1 defines a flow channel 3, an air inlet 31 is defined on a first end of the flow channel 3, and an air outlet 32 is defined on a second end of the flow channel 3. The air inlet 31 is configured to connect to the ventilator, and the air outlet 32 is configured to connect to a humidifier on a patient side. When a patent inhales, the check valve ensures that air only flows from the ventilator to the patient, and when the patient exhales, the check valve ensures that the air does not flow back into the ventilator from the check valve.

The flow guide assembly 2 is disposed in the flow channel 3. The flow guide assembly 2 is configured to guide a flow direction of the air, which is a key structure to prevent the air from flowing back into the ventilator.

In one optional embodiment, the flow guide assembly 2 comprises a first baffling sleeve 21 and a second baffling sleeve 22. The first baffling sleeve 21 and the second baffling sleeve 22 are disposed in an axial direction of the flow channel 3 in sequence. In another optional embodiment, the flow guide assembly 2 comprises at least two first baffling sleeves 21 and at least two second baffling sleeves 22. The at least two first baffling sleeves 21 and the at least two second baffling sleeves 22 are alternatively disposed in the axial direction of the flow channel 3. For example, a first one of the at least two first baffling sleeves 21, a first one of the at least two second baffling sleeves 22, a second one of the at least two first baffling sleeves 21, and a second one of the at least two second baffling sleeves 22 are disposed in sequence, alternatively, the first one of the at least two second baffling sleeves 22, the first one of the at least two first baffling sleeves 21, the second one of the at least two second baffling sleeves 22, and the second one of the at least two first baffling sleeves 21 are disposed in sequence. The present disclosure takes an example that the flow guide assembly 2 comprises the first baffling sleeve 21 and the second baffling sleeve 22 for further illustration.

Specifically, a first flow passing opening 212 is defined in the first baffling sleeve. One side of the first baffling sleeve 31 away from the first flow passing opening 212 is inclined toward the air outlet 32. One side of the second baffling sleeve 22 is inclined toward the air outlet 32. The second baffling sleeve 22 faces the first flow passing opening 212. A projection of the second baffling sleeve 22 on a horizontal cross section of the flow channel 3 completely overlaps a projection of the first flow passing opening 212 on the horizontal cross section of the flow channel 3, so the air is guided to the air outlet 32 from the air inlet 31 and is prevented from flowing back to the air inlet 31.

Furthermore, the first baffling sleeve 21 comprises a first baffling plate 211 and at least one first rectifying plate 213. Since most of flow path structures on the market are circular, a circular flow path is introduced as a basic design in the embodiment, but flow paths of other shapes should be included within the protection scope of the present disclosure. The first baffling plate 211 is arcuate. A curved side of the first baffling plate 211 is connected to an inner wall of the first baffling sleeve 21. A flat side of the first baffling plate 211 is disposed in the first baffling sleeve 21. An opening is formed between the flat side of the first baffle 211 and the inner wall of the first baffling sleeve 21, and the opening is the first flow passing opening 212.

In the embodiment, the first baffling plate 211 is arc-shaped. An outer arc surface of the first baffling plate 211 faces the air inlet 31, and an inner arc surface of the first baffling plate 211 faces the air outlet 32. The first baffling plate 211 is designed to have a curved structure to well guide the air, reduce a resistance of air intake of the ventilator, and ensure smooth breathing of the patient. In other alternative embodiments, the first baffling plate 211 may also be designed as a flat plate. Although the flat plate also guides the air, an air resistance thereof is relatively large, which is not conducive to the patient's inhalation. The first baffling plate 211 is close to the air inlet 31, and the at least one first rectifying plate 213 is close to the air outlet 32. The at least one first rectifying plate is located in a middle of the first baffling sleeve 21, so two openings, which are respectively a second flow passing opening 214 and a third flow passing opening 215, are defined between the at least one first rectifying plate 213 and an inner wall of the first baffling sleeve 21. The second flow passing opening 214 faces the first flow passing opening 212, and the third flow passing opening 215 faces the first baffling plate 211. In this way, the second flow passing opening 214 does not affect flow of the air from the first flow passing opening 212, and an arrangement of the third flow passing opening 215 ensures that when the air flows in from the air outlet 32, a portion of the air contacts the inner arc surface of the first baffling plate 211. The inner arc surface of the first baffling plate 211 then guides the portion of the air entering from the air outlet 32 to the second flow passing opening 214, and the second flow passing opening 214 guides the portion of the air out of the air inlet 31. Therefore, an arrangement of the at least one first rectifying plate 213 not only ensures that the first baffling plate 211 has a good effect of guiding air, but also divides the air from the air outlet 32 to avoid a noise caused by huge impact caused by entering and exiting of the air from the flow channel, which plays an excellent role in noise reduction to a certain extent, improves service life of the ventilator, and reduces a failure rate of the ventilator.

Furthermore, the second baffling sleeve 22 in the present disclosure may adopt a same design idea or different design ideas as the first baffling sleeve 21. In the embodiment, in order to reduce design cost and manufacturing cost, the second baffling sleeve 22 and the first baffling sleeve 21 adopts a same structure. The second baffling sleeve 22 and the first baffling sleeve 21 only have a certain difference in an installation angle. In order to ensure that the second baffling sleeve 22 faces to the first flow passing opening 212, the first baffling sleeve 21 in the embodiment is spaced apart from the second baffling sleeve 22, An deviation between an axis of the first baffling sleeve 21 and an axis of the second baffling sleeve 22 is 180 degrees, ensuring that the second baffling sleeve 22 completely cover the first flow passing opening 212. Specifically, the second baffling sleeve 22 comprises a second baffling plate 221 and at least one second rectifying plate 223. The second baffling plate 221 is arcuate. A curved side of the second baffling plate 221 is connected to an inner wall of the second baffling sleeve 22. A flat side of the second baffling plate 221 is disposed in the second baffling sleeve 22. An opening is formed between the flat side of the second baffling plate 221 and the inner wall of the second baffling sleeve 22, and the opening thereof is the fourth flow passing opening 222, In the embodiment, the second baffling plate 221 is arc-shaped. An outer arc surface of the second baffling plate 221 faces the first baffling plate 211, and an inner arc surface of the second baffling plate 221 faces the air outlet 32. The second baffle 211 is designed to have a curved structure to well guide the air, reduce the resistance of the air intake of the ventilator, and ensure smooth breathing of the patient. In other alternative embodiments, the second baffling plate 221 may also be designed as the flat plate. Although the flat plate also guides the air, the air resistance is relatively large, which is not conducive to the patient's inhalation. The second baffling plate 221 is close to the first baffling plate 211, and the at least one second rectifying plate 223 is close to the air outlet 32 and faces the first flow passing opening 212, and the fourth flow passing opening 222 faces the first baffling sleeve 21, so the first flow passing opening 212 and the fourth flow passing opening are staggered, and the air from the first flow passing opening 212 is guided out from the fourth flow passing opening 222.

The at least one second rectifying plate is close to the air outlet 32 and is located in a middle of the second baffling sleeve 22, so two openings, which are respectively a fifth flow passing opening 224 and a sixth flow passing opening 225, are defined between the at least one second rectifying plate 223 and an inner wall of the second baffling sleeve 22. The fifth flow passing opening 224 faces the fourth flow passing opening 222, and the sixth flow passing opening 225 faces the second baffling plate 221. In this way, the fifth flow passing opening 224 does not affect flow of the air from the fourth flow passing opening 222, and an arrangement of the sixth flow passing opening 225 ensures that when the air flows in from the air outlet 32, a portion of the air contacts the inner arc surface of the second baffling plate 221. The inner arc surface of the second baffling plate 221 then guides the portion of the air entering from the air outlet 32 to the fifth flow passing opening 224, and the fifth flow passing opening 224 guides the portion of the air out. Therefore, an arrangement of the at least one second rectifying plate 223 not only ensures that the second baffling plate 221 has a good effect of guiding the air, but also divides the air from the air outlet 32 to avoid the noise caused by huge impact caused by entering and exiting of the air from one flow channel, which plays an excellent role in noise reduction to a certain extent, improves the service life of the ventilator, and reduces the failure rate of the ventilator.

It should be noted that in other embodiments, the first baffling plate 211 and/or the second baffling plate 221 may also be the flat plate.

Optionally, both an area of a projection of the first flow passing opening 212 and an area of a projection of the fourth flow passing opening 222 on the horizontal cross section of the flow channel 3 are less than one half of an area of the horizontal cross section of the flow channel 3, ensuring that when the second baffling sleeve 22 and the first baffling sleeve 21 adopt the same structure, the first flow passing opening 212 faces the second baffling plate 221 and the fourth flow passing opening 222 faces the first baffling plate 211, which greatly reduces accuracy of design and installation, ensures a baffle for the air entering the air outlet 32, and prevents the air from flowing back into an interior of the ventilator from the air inlet.

Furthermore, the housing assembly 1 and the flow guide assembly 2 are assembled in various styles according to actual requirement, e.g., the housing assembly 1 and the flow guide assembly 2 are integrated into one structure or are separated structures assembled with each other. In order to reduce assembly and design costs and achieve flexible assembly forms and collocations, an assembly structure of the housing assembly 1 and the flow guide assembly 2 is optimized in the present disclosure.

Figure 4:
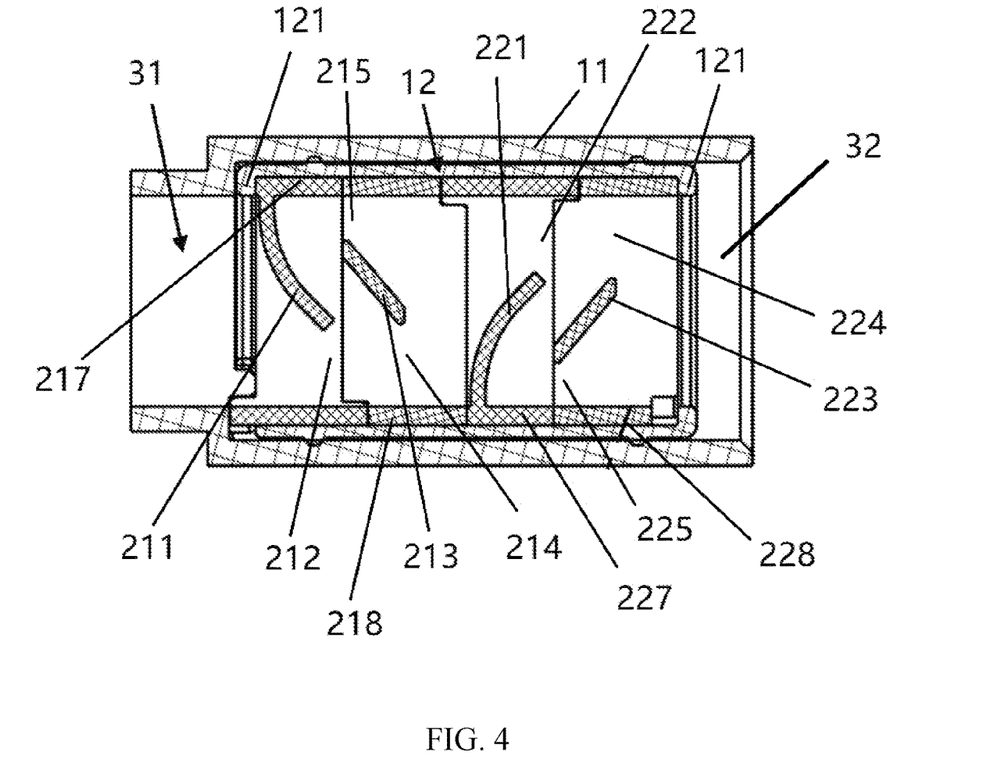
FIG. 4 is a cross-sectional schematic diagram of the check valve according to a second embodiment of the present disclosure.
Figure 5:
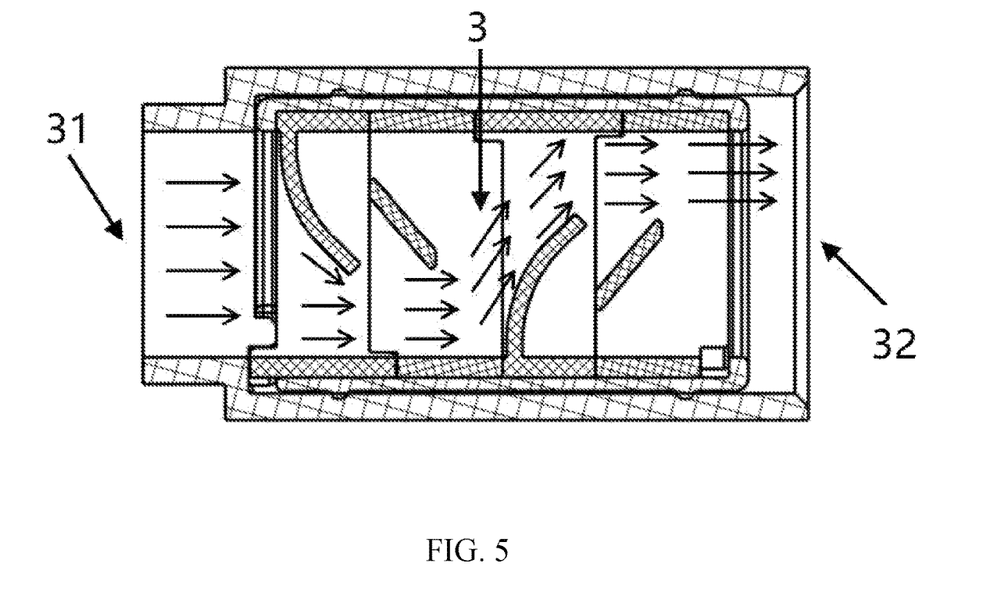
FIG. 5 is a schematic diagram showing an air flow state in the check valve of the present disclosure when a patient inhales.

As shown in FIGS. 4 and 5, when the air flows forward (i.e., from the air inlet 31 to the air outlet 32), the air first passes through the outer arc surface of the first baffling plate 211, the flow direction of the air changes, and the air flows along the outer arc surface of the first baffling plate 211. Then, when the air flow contacts the at least one first rectifying plate, the flow direction of the air does not change. Then, the air contacts the second baffling plate 221, the flow direction of the air changes, the air flows along the outer arc surface of the second baffling plate 221, and the air flows out of the air outlet 32 after contacting the second baffling plate 221.

Figure 6:
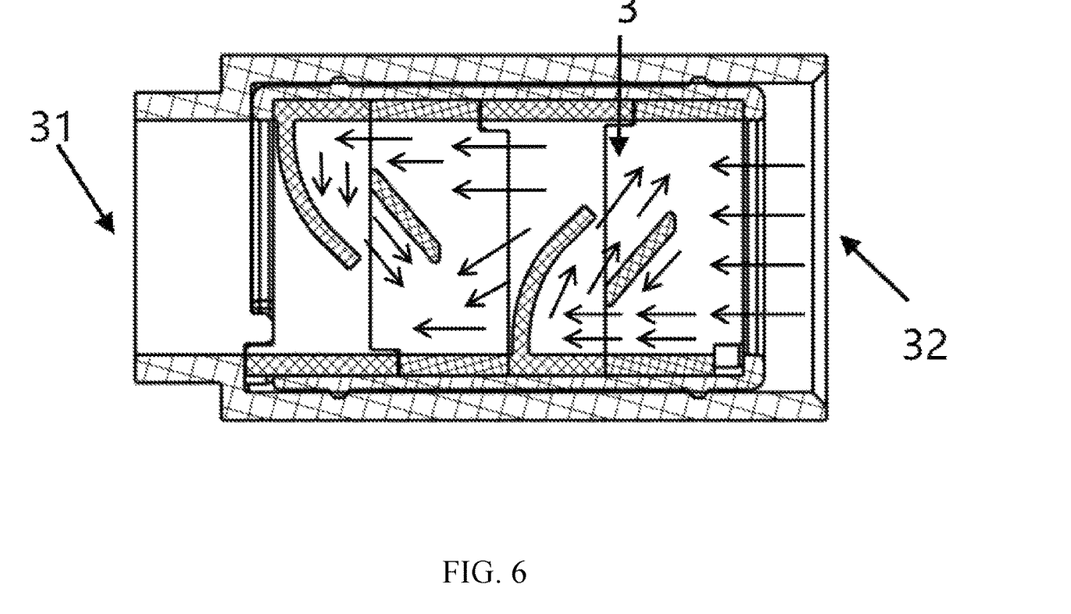
FIG. 6 is a schematic diagram of an air flow state in the check valve of the present disclosure when the patient exhales.

As shown in FIGS. 4 and 6, when the air flows in reverse (from the air outlet 32 to the air inlet 31), the air first flows through the at least one second rectifying plate 223, the air is divided into two portion by the second rectifying plate 223, a first portion of the air flows through the sixth flow passing opening 225 and then flows through the second baffling plate 221. The second baffling plate 221 changes the flow direction of the first portion of the air, so the first portion of the air flows along the inner arc surface of the second baffling plate 221. When the first portion of the air flows out along the second baffling plate 221, the first portion of the air meets current air flowing in reverse. Since the second baffling plate 221 changes the flow direction of the first portion of the air, the first portion of the air has a forward flow velocity. Therefore, when the first portion of the air meets the current air flowing in reverse, a flow velocity of the current air flowing in reverse is partially counteracted, a resistance of the current air flowing in reverse increases, and the current air flowing to the air inlet 31 decreases. A second portion of the air flow flowing in reverse flows to the first baffling sleeve 21 through the fourth flow passing opening 222 and the fifth flow passing opening 224. When the second portion of the air flow flowing in reverse flows through the at least one first rectifying plate 213 and the first baffling plate 211, the flow velocity of the current air flowing in reverse is further counteracted, the resistance of the current air flowing in reverse further increases, and the current air finally flowing to the air inlet 31 decreases to an acceptable range after the air changes directions and counteracts each other many times, so that the air only flows forward and cannot flow in reverse.

The present disclosure effectively prevents backflow of the air, prevents the air flowing from the humidifier and the patient from flowing backward into the ventilator, effectively prevents water vapor and germs from invading the ventilator, and protects internal components of the ventilator from being corroded by the water vapor or germ contamination. Further, compared with the prior art, the check valve effectively reduces the noise of the ventilator, effectively reduces a failure rate of the check valve, improves operation stability of the ventilator, and reduces maintenance cost of the ventilator.

Specifically, as shown in FIGS. 2 and 4, the housing assembly 1 comprises a pipe sleeve 11 and a sealing sleeve 12.

The pipe sleeve 11 is the outermost layer of the check valve. The pipe sleeve 11 has high toughness and hardness, and provides good protection for a whole structure of the check valve. The sealing sleeve 12 is made of silicone, and the sealing sleeve 12 is disposed in the pipe sleeve 11. A sealing ring is disposed between the sealing sleeve 12 and the pipe sleeve 11. The sealing ring improves a cooperation degree between the sealing sleeve 12 and the pipe sleeve 11 and seals a gap between the sealing sleeve 12 and the pipe sleeve 11 to form a good sealing effect. Further, the sealing ring avoids vibration of the sealing sleeve 12 in the gap, thereby avoiding generation of the noise. The flow channel is defined in the sealing sleeve 12. The sealing sleeve 12 ensures sealing of the flow channel 3. The flow guide assembly 2 is sleeved in the sealing sleeve 12 to realize the one-way flow of the air. By such arrangements, when assembling, it is only necessary to adjust a position of the flow guide assembly 2 first, sleeve the flow guide assembly 2 in the sealing sleeve 12, and finally fix the sealing sleeve 12 in the pipe sleeve 11 to complete the assembly of the check valve. By adopting such a package method, components of the check valve are detachable, and a user is able to flexibly disassemble or replace the components according to needs, which not only successfully reduces design and manufacturing costs, but also realizes low-cost maintenance in a later period.

Furthermore, annular bulges 121 are disposed on two ends of the sealing sleeve 12. The flow guide assembly 2 is disposed between the annular bulges 121. The annular bulges 121 limit the flow guide assembly 2 in an axis direction of the flow guide assembly 2. The annular bulges 121 prevent the flow guide assembly 2 from moving when the air flows.

Figure 3:
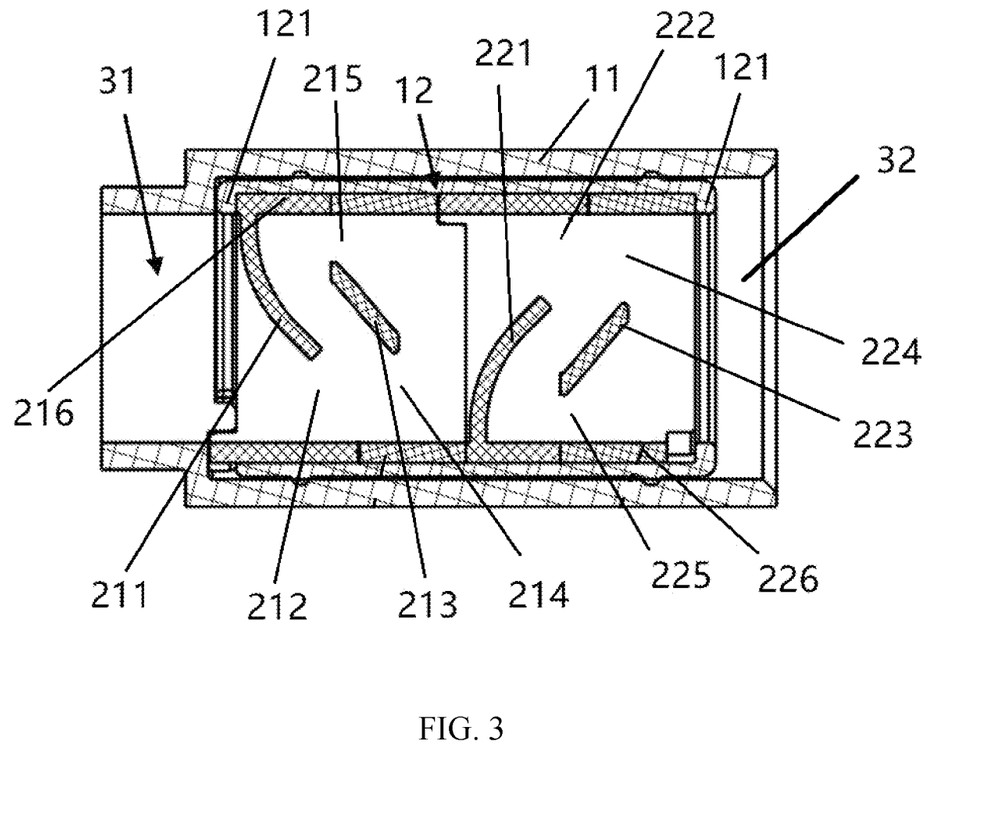
FIG. 3 is a cross-sectional schematic diagram of the check valve according to a first embodiment of the present disclosure.

Furthermore, as shown in FIG. 3, in a first embodiment, the flow guide assembly 2 is divided into modules. The first baffling sleeve 21 comprises a first outer ring 216, a first baffling plate 211, and a first rectifying plate 213. The first baffling plate 211 and the first rectifying plate 213 are disposed on an inner side of the first outer ring 216. The second baffling sleeve 22 comprises a second outer ring 226, a second baffling plate 221, and a second rectifying plate 223. The second baffling plate 221 and the second rectifying plate 223 are disposed on an inner side of the second outer ring 226. An end surface of the first outer ring 216 abuts against an end surface of the second outer ring 226 for positioning, and the first outer ring 216 and the second outer ring 226 are installed in the sealing sleeve 12 to form the flow guide assembly 2, so as to realize the function of the check valve. In the embodiment, the first baffling sleeve 21 and the second baffling sleeve 22 are respectively modularized, so the user is able to freely select the number and arrangement of the first baffling sleeve 21 and the second baffling sleeve 22 according to actual situations. Further, it also facilitates later replacement of the first baffling sleeve 21 and/or the second baffling sleeve 22.

Furthermore, as shown in FIGS. 2, 4, 7, and 8, in a second embodiment, it is also possible to modularize the first baffling sleeve 21 and the second baffling sleeve 22 on a basis that the first baffling sleeve 21 and the second baffling sleeve 22 are modularized as mentioned above. Specifically, the first outer ring 216 comprises a first baffling outer ring 217 and a first rectifying outer ring 218. The first baffling plate 211 is disposed in the first baffling outer ring 217. The first rectifying plate 213 is disposed in the first rectifying outer ring 218. The second outer ring 226 comprises a second baffling outer ring 227 and a second rectifying outer ring 228. The second baffling plate 221 is disposed in the second baffling outer ring 227. The second rectifying plate 223 is disposed in the second rectifying outer ring 228.

Figure 7:
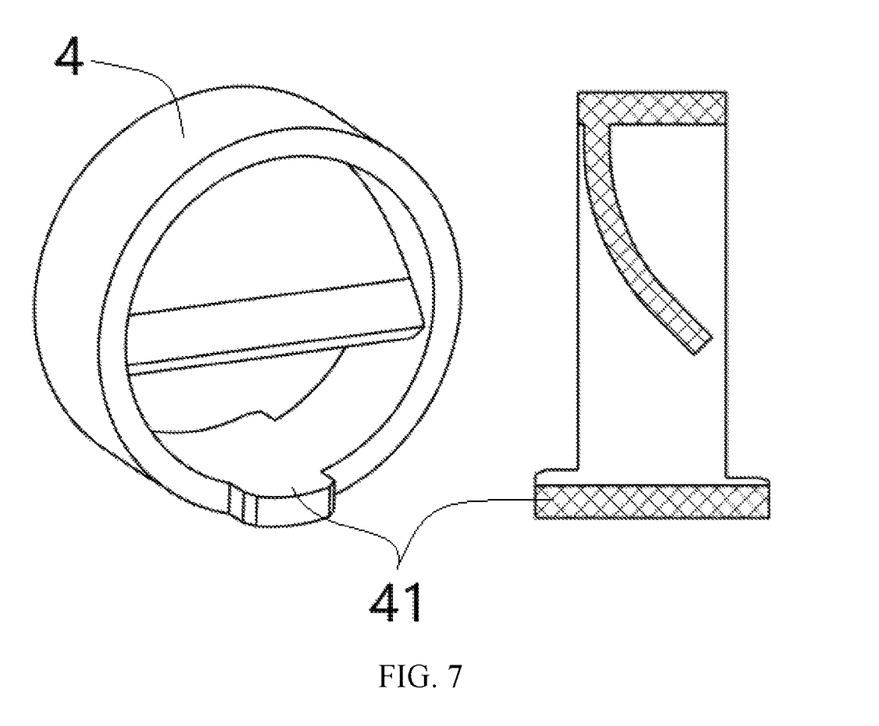
FIG. 7 is a schematic diagram of a baffling outer ring standard part of the check valve of the present disclosure.
Figure 8:
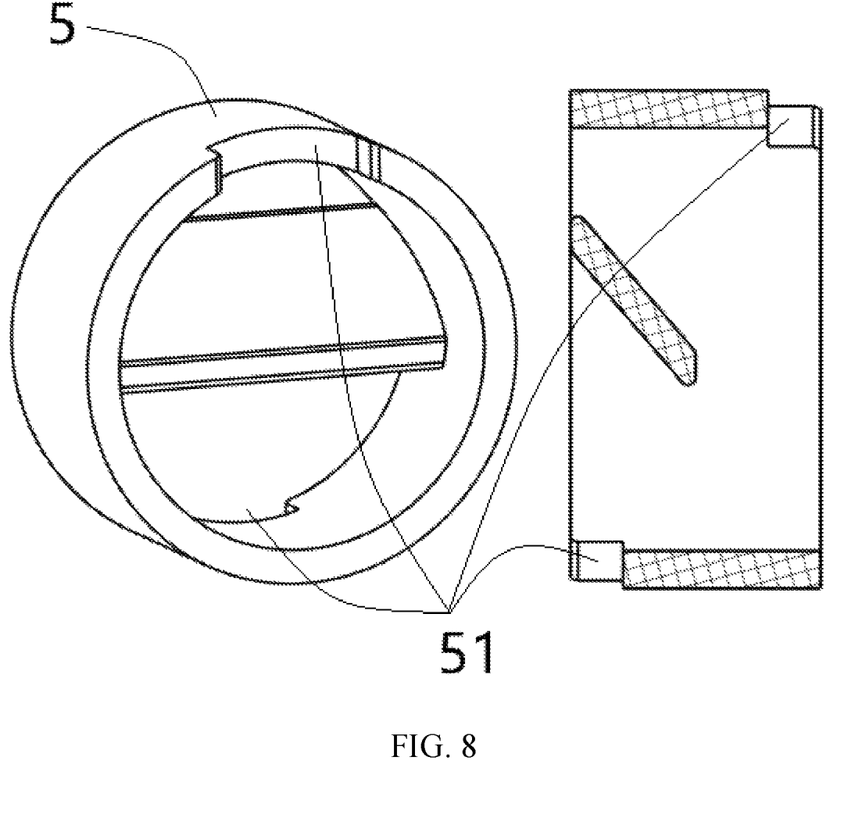
FIG. 8 is a schematic diagram of a rectifying outer ring standard part of the check valve of the present disclosure.

The first baffling outer ring 217 and the second baffling outer ring 227 are baffling outer ring standard parts 4. The first rectifying outer ring 218 and the second rectifying outer ring 228 are rectifying outer ring standard parts 5. When assembling, a deviation between an axis of the first baffling outer ring and an axis of the second baffling outer ring is made to be 180 degrees and a deviation between an axis of the first rectifying outer ring 218 and an axis of the second rectifying outer ring 228 a is 180 degrees. By such arrangement, one or more first baffling outer rings 217, one or more second baffling outer rings 227, one or more first rectifying outer rings 218, and one or more second rectifying outer rings 228 are freely selected and assembled. For example, at least two first rectifying outer rings 218 are connected to a rear end of one or at least two first baffling outer rings 217. Alternatively, at least two second rectifying outer rings 228 are connected to a rear end of one or at least two second baffling outer rings 227. By configuring the first baffling outer ring 217 and the second baffling outer ring 227 as the baffling outer ring standard parts 4 and configuring the first rectifying outer ring 218 and the second rectifying outer ring 228 as the rectifying outer ring standard parts 5, a flexible configuration of the flow guide assembly 2 is realized.

Furthermore, in order to conveniently fix positions of the first baffling sleeve 21 and the second baffling sleeve 22, each of the baffling outer ring standard parts 4 comprises two positioning protrusion 41 respectively disposed on two circumferential surfaces of each of the baffling outer ring standard parts 4. The two positioning protrusions 41 of each of the baffling outer ring standard parts 4 are symmetrically disposed with respect to a horizontal cross section of each of the baffling outer ring standard parts 4. Each of the rectifying outer ring standard parts 5 comprises two positioning grooves 51 respectively defined on two circumferential surfaces of each of the rectifying outer ring standard parts 5. The two positioning grooves 51 of each of the rectifying outer ring standard parts 5 are symmetrically disposed with respect to a horizontal cross section of each of the rectifying outer ring standard parts 5, and the two positioning grooves 51 of each of the rectifying outer ring standard parts are symmetrically disposed with respect to a vertical cress section of each of the rectifying outer ring standard parts if one of the two positioning grooves 51 of each of the rectifying outer ring standard parts is rotated 180 degrees in the axis direction.

When installing, a first one of the baffling outer ring standard parts 4 (the first baffling outer ring 217) abuts against one of the annular bulges 121 of the sealing sleeve 12, and then a first one of the rectifying outer ring standard parts 5 (the first rectifying outer ring 218) is sleeved in the sealing sleeve 12. Then a position of the first one of the rectifying outer ring standard parts 5 is adjusted. Specifically, a first one of the positioning grooves 51 of the first one of the rectifying outer ring standard parts 5 is engaged with one of the positioning protrusions 41 of the first one of the baffling outer ring standard parts 4 to realize the positioning of the first one of the baffling outer ring standard parts 4 and the first one of the rectifying outer ring standard parts 5. Then, a second one of the baffling outer ring standard parts 4 (the second baffling outer ring 227) is sleeved in the sealing sleeve 12, and one of the positioning protrusions 41 of the second one of the baffle outer ring standard parts 4 is engaged with a second one of the positioning grooves 51 of the first one of the rectifying outer ring standard parts 5. Then a second one of the rectifying outer ring standard part 5 (the second rectifying outer ring 228) is sleeved in the sealing sleeve 12 for positioning in a similar way, thereby completing the assembly of the check valve. The second baffling sleeve 22 is rotated 180 degrees with respect to the first baffling sleeve 21 during an assembly process, thereby playing a role of positioning and fool-proof, preventing misalignment during the assembly process, and improving assembly efficiency.

Foregoing descriptions are only optional embodiments of the present disclosure and are not intended to limit the present disclosure. Any modification, equivalent replacement, or improvement within the technical scope of the present disclosure should be included in the protection scope of the present disclosure.

What is claimed is:

1. A check valve for a ventilator, comprising:
a housing assembly, and
a flow guide assembly;
wherein the housing assembly defines a flow channel, and the flow channel defines an air outlet;
wherein the flow guide assembly is disposed in the flow channel; the flow guide assembly comprises a first baffling sleeve and a second baffling sleeve; the first baffling sleeve and the second baffling sleeve are disposed in an axial direction of the flow channel in sequence; a first flow passing opening is defined in the first baffling sleeve; one side of the first baffling sleeve away from the first flow passing opening is inclined toward the air outlet; one side of the second baffling sleeve is inclined toward the air outlet; the second baffling sleeve faces the first flow passing opening; a projection of the second baffling sleeve on a horizontal cross section of the flow channel completely overlaps a projection of the first flow passing opening on the horizontal cross section of the flow channel.

2. The check valve according to claim 1, wherein the flow channel further defines an air inlet; the first baffling sleeve comprises a first baffling plate; the first flow passing opening is formed between the first baffling plate and an inner wall of the first baffling sleeve; the first baffling plate is arc-shaped; an outer arc surface of the first baffling plate faces the air inlet, and an inner arc surface of the first baffling plate faces the air outlet.

3. The check valve according to claim 2, wherein the first baffling sleeve further comprises at least one first rectifying plate; the first baffling plate is close to the air inlet; the at least one first rectifying plate is close to the air outlet; the at least one first rectifying plate is located in a middle of the flow channel; a second flow passing opening is formed between a first side surface of the at least one first rectifying plate and the inner wall of the first baffling sleeve; a third flow passing opening is formed between a second side surface of the at least one first rectifying plate and the inner wall of the first baffling sleeve; the second flow passing opening faces the first flow passing opening, and the third flow passing opening faces the first baffling plate.

4. The check valve according to claim 1, wherein the second baffling sleeve comprises a second baffling plate; a fourth flow passing opening is formed between the second baffling plate and an inner wall of the second baffling sleeve; the second baffling plate is arc-shaped; an outer arc surface of the second baffling plate faces the air inlet, and an inner arc surface of the second baffling plate faces the air outlet.

5. The check valve according to claim 4, wherein the second baffling sleeve further comprises at least one second rectifying plate; the second baffling plate is close to an air inlet; the at least one second rectifying plate is close to the air outlet; the at least one second rectifying plate is located in a middle of the flow channel; a fifth flow passing opening is formed between a first side surface of the at least one second rectifying plate and the inner wall of the second baffling sleeve; a sixth flow passing opening is formed between a second surface of the at least one second rectifying plate and the inner wall of the second baffling sleeve; the fifth flow passing opening faces the fourth flow passing opening, and the sixth flow passing opening faces the second baffling plate.

6. The check valve according to claim 4, wherein both an area of a projection of the first flow passing opening and an area of a projection of the fourth flow passing opening on the horizontal cross section of the flow channel are less than one half of an area of the horizontal cross section of the flow channel.

7. The check valve according to claim 1, wherein the housing assembly comprises a pipe sleeve and a sealing sleeve; positioning protrusions are disposed on an outer side of the sealing sleeve; annular bulges are disposed on two ends of the sealing sleeve; the flow guide assembly is disposed between the annular bulges.

8. The check valve according to claim 7, wherein the first baffling sleeve comprises a first outer ring, a first baffling plate, and a first rectifying plate; wherein the first baffling plate and the first rectifying plate are disposed on an inner side of the first outer ring; the first baffling plate and the first rectifying plate are configured to guide air;
wherein the second baffling sleeve comprises a second outer ring, a second baffling plate, and a second rectifying plate; the second baffling plate and the second rectifying plate are disposed on an inner side of the second outer ring; the second baffling plate and the second rectifying plate are configured to guide the air;
wherein an end surface of the first outer ring abuts against an end surface of the second outer ring; the first outer ring and the second outer ring are installed in the sealing sleeve.

9. The check valve according to claim 8, wherein the first outer ring comprises a first baffling outer ring and a first rectifying outer ring; the first baffling plate is disposed in the first baffling outer ring; the first rectifying plate is disposed in the first rectifying outer ring;
wherein the second outer ring comprises a second baffling outer ring and a second rectifying outer ring; the second baffling plate is disposed in the second baffling outer ring; the second rectifying plate is disposed in the second rectifying outer ring;
wherein the first baffling outer ring and the second baffling outer ring are baffling outer ring standard parts; a deviation between an axis of the first baffling outer ring and an axis of the second baffling outer ring is 180 degrees; the first rectifying outer ring and the second rectifying outer ring are rectifying outer ring standard parts; a deviation between an axis of the first rectifying outer ring and an axis of the second rectifying outer ring is 180 degrees.

10. The check valve according to claim 9, wherein each of the baffling outer ring standard parts comprise two positioning protrusions respectively disposed on two circumferential surfaces of each of the baffling outer ring standard parts; the two positioning protrusions of each of the baffling outer ring standard parts are symmetrically disposed with respect to a horizontal cross section of each of the baffling outer ring standard parts; each of the rectifying outer ring standard parts comprise two positioning grooves respectively defined on two circumferential surfaces of each of the rectifying outer ring standard parts; the two positioning grooves of each of the rectifying outer ring standard parts are symmetrically disposed with respect to a horizontal cross section of each of the rectifying outer ring standard parts, and the two positioning grooves of each of the rectifying outer ring standard parts are symmetrically disposed with respect to a vertical cress section of each of the rectifying outer ring standard parts if one of the two positioning grooves of each of the rectifying outer ring standard parts is rotated 180 degrees in an axis direction.

* * * * *